(12) United States Patent
Cavallazzi et al.

(10) Patent No.: US 8,496,665 B2
(45) Date of Patent: Jul. 30, 2013

(54) DRILL SLEEVE

(75) Inventors: Cesare Cavallazzi, Miramar, FL (US);
Marcus Bourda, Miami, FL (US);
Sravanthi Avuthu, Miramar, FL (US)

(73) Assignee: Biomet C.V., Gibraltar (GI)

( * ) Notice: Subject to any disclaimer, the term of this patent is extended or adjusted under 35 U.S.C. 154(b) by 1262 days.

(21) Appl. No.: 12/030,371

(22) Filed: Feb. 13, 2008

(65) Prior Publication Data

US 2009/0204121 A1  Aug. 13, 2009

(51) Int. Cl.
| | |
|---|---|
| *A61B 17/00* | (2006.01) |
| *A61B 17/58* | (2006.01) |
| *A61B 17/60* | (2006.01) |
| *A61F 2/00* | (2006.01) |
| *B23B 51/00* | (2006.01) |
| *B23G 5/00* | (2006.01) |
| *B23D 77/00* | (2006.01) |
| *B27G 15/00* | (2006.01) |
| *B23B 49/00* | (2006.01) |
| *B23B 49/02* | (2006.01) |

(52) U.S. Cl.
USPC ............ 606/96; 606/80; 408/202; 408/241 B; 408/241 S

(58) Field of Classification Search
USPC ... 606/96, 80; 408/202, 241 B, 241 S; 433/75
See application file for complete search history.

(56) References Cited

U.S. PATENT DOCUMENTS

| | | | |
|---|---|---|---|
| 3,620,637 A * | 11/1971 | Brown | 408/202 |
| 4,019,827 A * | 4/1977 | Christianson et al. | 408/202 |
| 4,033,043 A | 7/1977 | Cunningham | |
| 4,039,266 A * | 8/1977 | O'Connell | 408/202 |
| 4,341,206 A | 7/1982 | Perrett et al. | |
| 5,013,318 A | 5/1991 | Spranza, III | |
| 5,112,337 A | 5/1992 | Paulos et al. | |
| 5,122,146 A | 6/1992 | Chapman | |
| 5,354,300 A | 10/1994 | Goble et al. | |
| 5,409,493 A | 4/1995 | Greenberg | |
| 5,429,504 A * | 7/1995 | Peltier et al. | 433/165 |
| 5,458,654 A | 10/1995 | Tepic | |
| 5,851,207 A * | 12/1998 | Cesarone | 606/86 B |
| 5,895,389 A | 4/1999 | Schenk | |
| 5,899,908 A | 5/1999 | Kuslich et al. | |
| 6,514,258 B1 * | 2/2003 | Brown et al. | 606/80 |
| 6,562,046 B2 | 5/2003 | Sasso | |
| 6,729,037 B2 | 5/2004 | White | |

(Continued)

FOREIGN PATENT DOCUMENTS

| | | |
|---|---|---|
| DE | 3800482 | 7/1989 |
| WO | WO98/53942 | 12/1998 |

*Primary Examiner* — Kevin T Truong
*Assistant Examiner* — David Bates
(74) *Attorney, Agent, or Firm* — Gordon & Jacobson, PC

(57) ABSTRACT

A drill sleeve is provided for guiding a bone drill in alignment with the screw holes and drill guides. The drill sleeve includes a cylindrical body having a first end, a second end and a longitudinal axis extending therebetween. The cylindrical body includes a longitudinal bore therethrough that is sized for passage of a bone drill. The drill sleeve also includes a frictional retaining element for exerting a bearing force against the surface of the bone drill, such that the frictional retaining element may support at least the weight of the drill sleeve on the bone drill. The bone drill has graduated indicia, and a portion of the drill sleeve may be referenced relative to the indicia so as to be used as a depth gauge for determining the length of a drilled hole in order to select a screw fastener having the appropriate length.

21 Claims, 15 Drawing Sheets

U.S. PATENT DOCUMENTS

| | | |
|---|---|---|
| 7,033,363 B2 | 4/2006 | Powell |
| 7,163,542 B2 | 1/2007 | Ryan |
| 7,165,336 B2 | 1/2007 | Kim |
| 7,299,561 B2 | 11/2007 | Castaneda |
| 7,513,722 B2 * | 4/2009 | Greenberg et al. ............ 408/202 |
| 2005/0234467 A1 | 10/2005 | Rains |
| 2006/0190001 A1 * | 8/2006 | Powell ............................ 606/96 |
| 2006/0207118 A1 | 9/2006 | Kim |
| 2006/0207119 A1 | 9/2006 | Kim |
| 2006/0264956 A1 | 11/2006 | Orbay |
| 2006/0269370 A1 * | 11/2006 | Cornwell ................... 408/115 R |
| 2007/0088365 A1 | 4/2007 | Ruhling |
| 2007/0099150 A1 * | 5/2007 | Muller et al. ................. 433/165 |
| 2007/0119063 A1 | 5/2007 | Kim |
| 2007/0206996 A1 * | 9/2007 | Bharadwaj et al. ........... 408/202 |
| 2007/0298375 A1 * | 12/2007 | Hirsch et al. ................. 433/165 |

\* cited by examiner

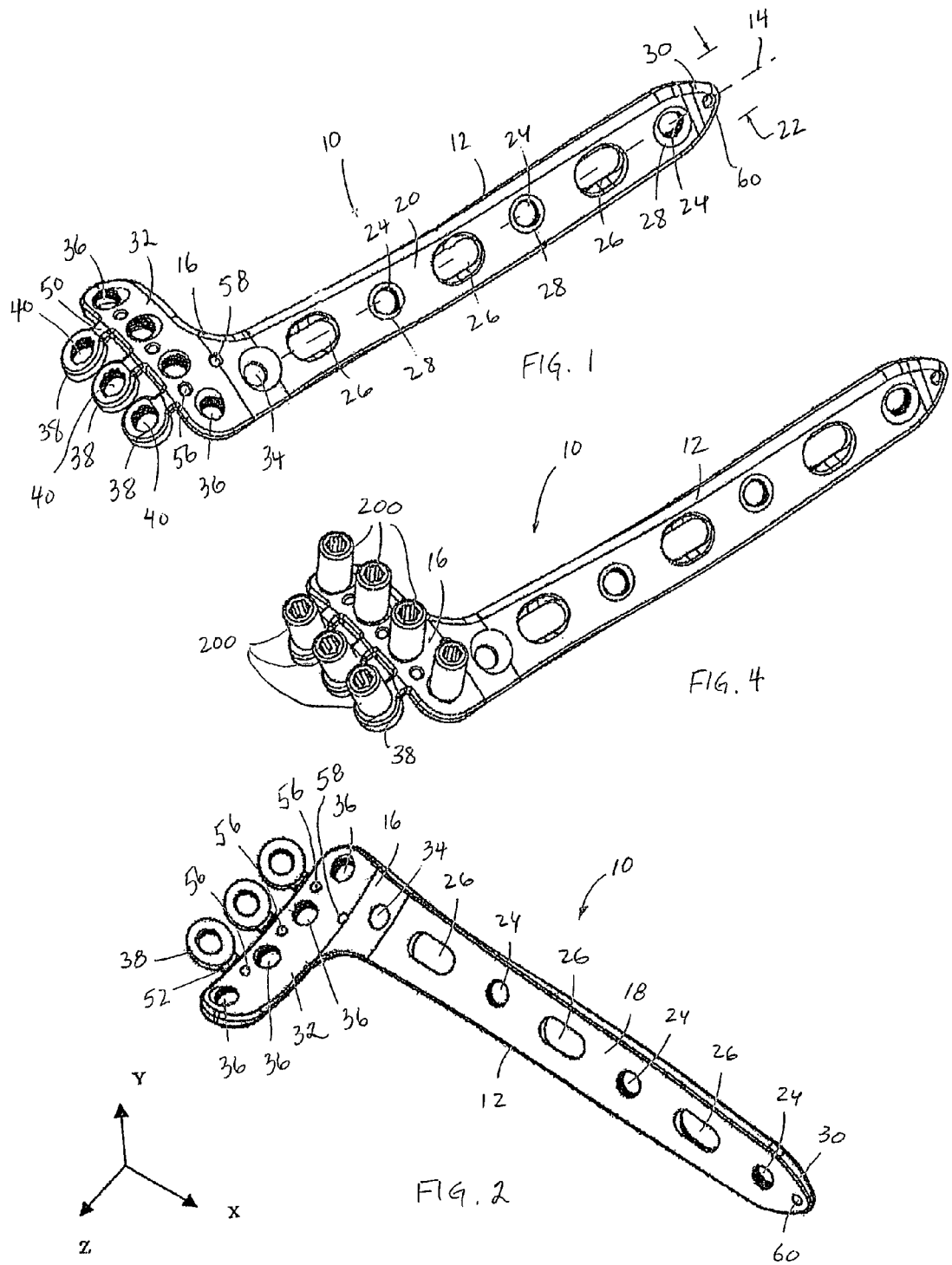

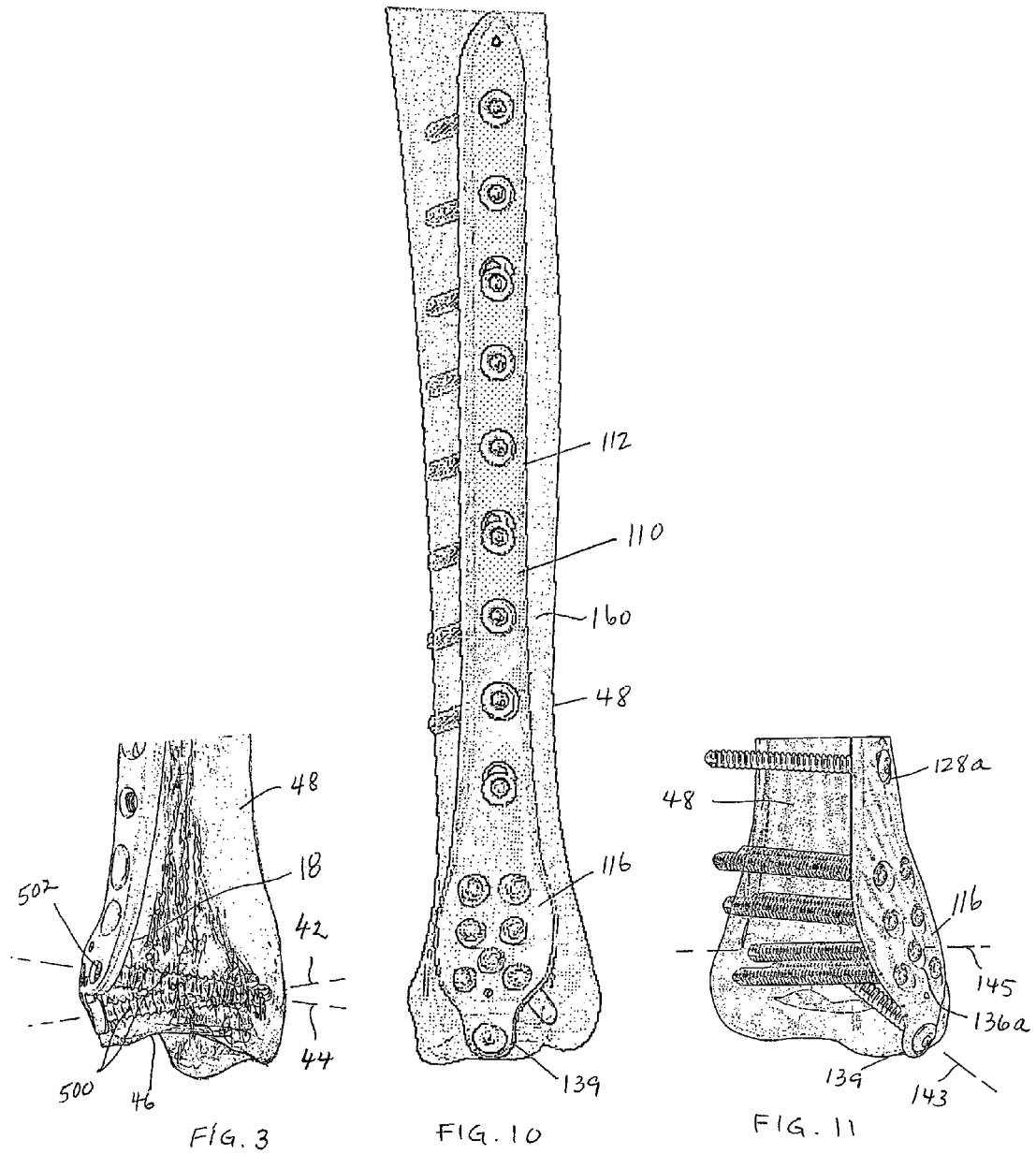

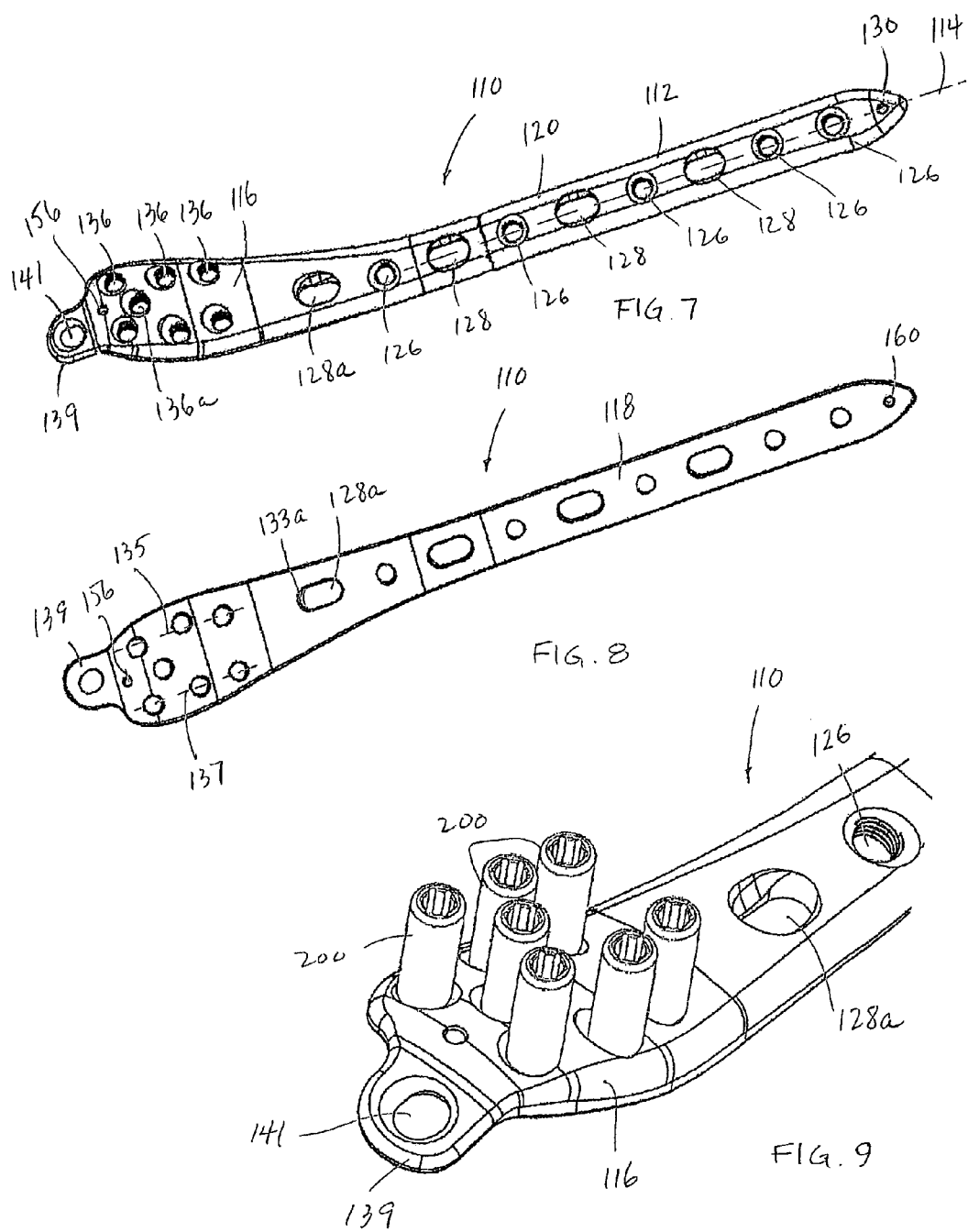

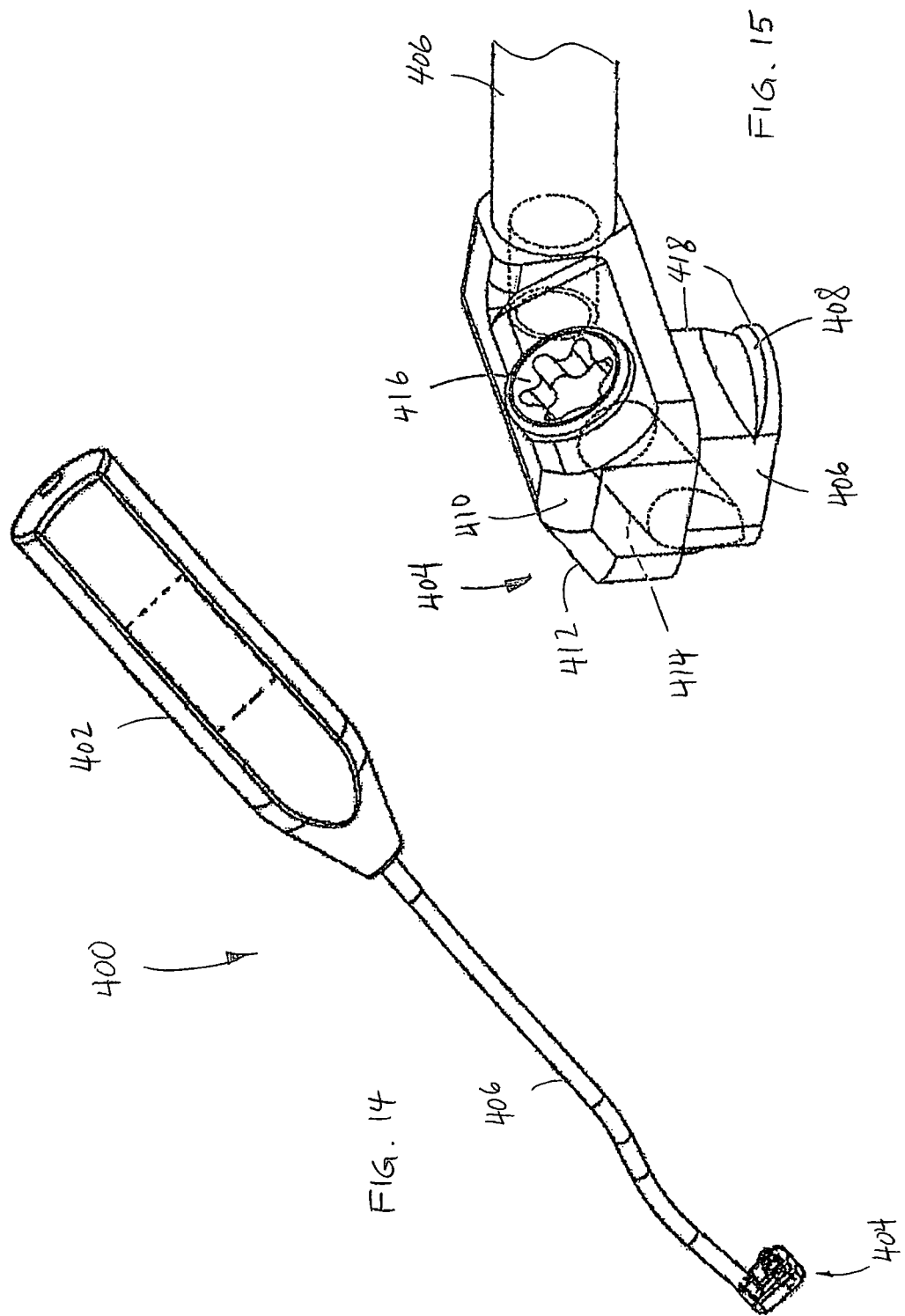

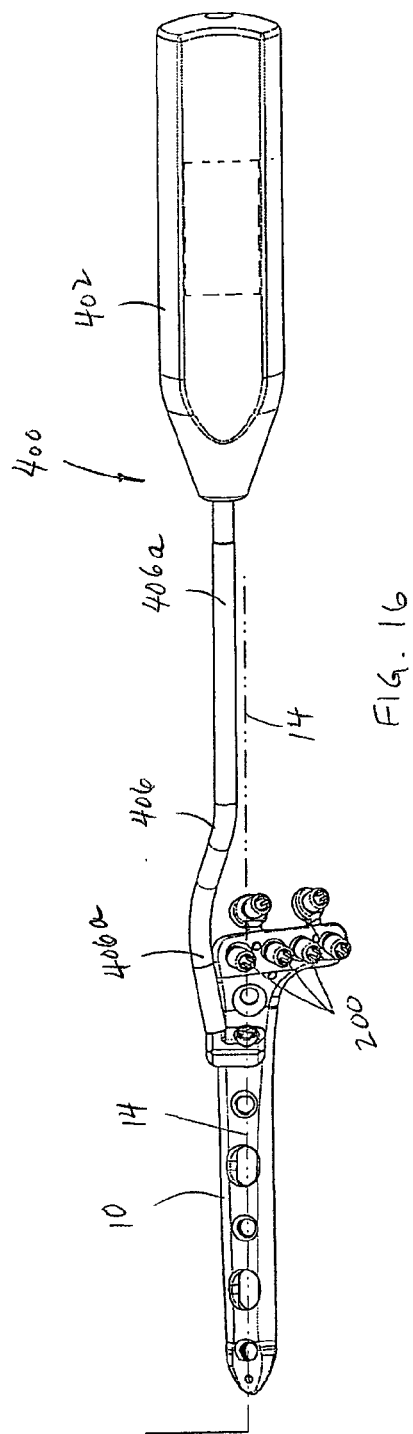
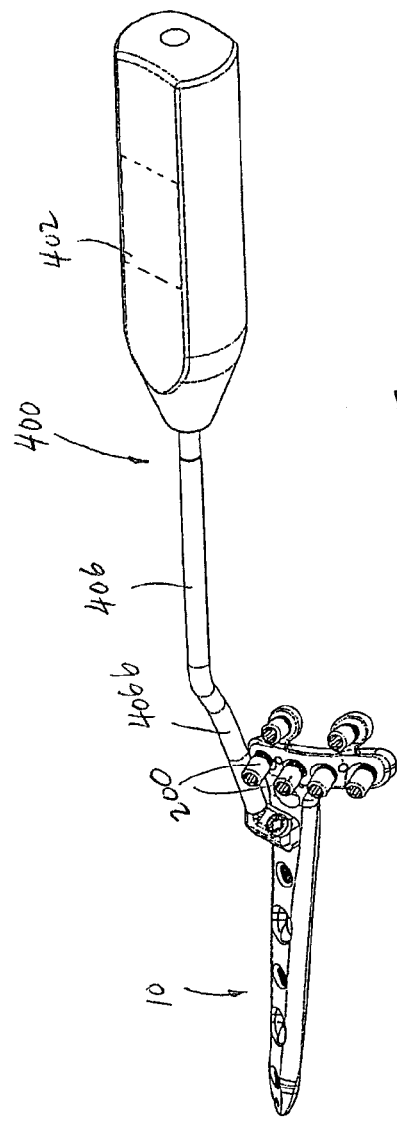

DRILL SLEEVE

BACKGROUND OF THE INVENTION

1. Field of the Invention

This invention relates broadly to surgical devices and methods for the internal fixation of fractured bones, and more particularly to bone plates, fasteners and tools therefor.

2. State of the Art

Fractures of the distal tibia include tibial plafond (or pilon) fractures and ankle fractures. These "high energy" fractures are typically caused by axial loading of the ankle joint, due to falls, motor vehicle accidents and sports. The more common ankle fractures are usually repaired with screw fixation. However, as with any kind of intra-articular fracture, distal tibial fractures are notoriously difficult to treat and are associated with a high complication rate.

Tibial plafond fractures are relatively uncommon (less than one percent of all fractures). Still, several thousands of people suffer annually. The type of fracture depends on the degree of comminution and displacement. Treatments of plafond fractures include external fixation, plating and nailing.

The same four basic principles for internal fixation apply to the distal tibia fracture as for any other bone fracture. These principles are proper anatomic reduction, stable fixation, preservation of blood supply and early, active mobilization. Before plating the distal tibia, surgeons usually wait several days after the injury was incurred to allow the soft tissues to heal and the swelling to decrease. Normally they will plate the distal fibula immediately if it is also fractured. After plating the distal tibia, weight bearing is normally not allowed for several days.

Currently there is some controversy among orthopedic surgeons concerning the management of tibial plafond fractures as to whether to use internal plating or external fixation. The trend in recent years has shifted to external fixation due to complications associated with plating. Major complications include skin sloughing and infection. These relate to the significant soft tissue injury associated with the fracture. Other less common complications include non-union, malunion, osteoarthritis and arthrodesis.

Current plates have been developed to try to reverse that trend. The plates include Synthes LCP Anterolateral and Medial Distal Tibia Plates 3.5, Smith & Nephew Peri-Loc Anterolateral and Medial Tibia Locking Plates, and Zimmer Periarticular Distal Tibia Locking Plates. The current plates are made of stainless steel. While the plates are pre-contoured for a non-specific bone, the systems are provided with bending tools that can be extended through the holes of a respective plate or gripped pliers that externally hold the plate to effect additional bending of the plate. However, such bending must be done with the plate off the bone in a manner in which it is difficult to approximate the shape of the plate to a specific bone without significant trial and error. In addition, the medial plates of current distal tibia fixation systems have limited support for the subchondral bone of the articular surface. Moreover, any such support is either at a predetermined fixed angle using fixed angle screws in threaded holes or variable angle and under compression. Where surgeons want to use a distal tibia plating system with a fixed angle construct to support the fracture, fixed angle constructs do not conform to the anatomy or have the required strength to support distal tibia fractures. Thus, these plate systems are unacceptable in their limitations. In addition, when attaching a bone plate to a fractured bone during an internal fixation procedure, surgeons often must select bone screws and/or pegs having sufficient length for bicortical engagement, yet not so long that the fastener tip extends through joint bearing surfaces or into soft tissues distal to the bone. Surgeons typically determine the appropriate bone screw length after drilling a hole into bone by: (1) removing the bone drill and inserting some type of depth gauge into the drilled hole, or (2) reading graduated indicia on either the bone drill or an ancillary device used in combination with the bone drill while the drill is still fully inserted into the drilled hole. The first approach normally is more time-consuming than the second. However the second approach typically involves the need for the surgeon to stoop over and peer into the surgical site in order to read indicia on the drill or ancillary device.

SUMMARY OF THE INVENTION

A distal tibia plating system according to the invention provides improvements in internal fixation of distal tibia fractures. The plating system includes an anterolateral plate and a medial plate. Each of the plates include a proximal shaft portion and a distal head portion. The head portion is provided with a plurality of threaded first holes and a non-threaded second hole. Each threaded first hole is configured for receiving at least one of a plurality of fastener types and is preferably chamfered to permit the head of the fastener to seat low in the hole. Each of the fastener holes is preferably provided with a pre-assembled drill guide that is adapted to guide a drill into bone in axial alignment with the fastener hole and optionally for use with one member of a pair of bending instruments.

The anterolateral plate is a low profile plate including a shaft defining a longitudinal axis and a laterally extending distal head. The shaft includes both threaded first fastener holes and compression slots along its length. The head includes a first row of four threaded fastener holes arranged transversely to the longitudinal axis, a non-threaded compression screw hole, and a plurality of distal tabs. Each tab includes a ring with a single threaded fastener hole and a bridge that couples the ring to the distal end of the plate. The hole in each tab is not necessarily chamfered, but the holes in the tabs are capable of receiving the same fasteners as the first row of threaded fastener holes. The holes in the tabs are aligned to define a second row of threaded holes. The first and second rows of threaded holes are approximately parallel and the axes of the threaded holes of the first row are staggered with respect to the axes of the threaded holes of the second row. The tabs are preferentially oriented such that the axes of threaded holes of the first row converge and pass between the axes of the threaded holes of the second row, with fasteners inserted therethrough thereby forming a load-bearing scaffold to support the articular surface of the distal tibia. The bridge of each tab is configured to bend preferentially in a desired direction, such that an axis of a fastener hole of a tab will not intersect the axis of a fastener hole in the first row of the distal head portion. In this manner, one or more of the tabs can be easily reconfigured relative to the remainder of the plate, e.g., to capture the distal rim of the tibia, to capture a specific bone fragment or buttress and support a desired area, while the plate is on the bone. This is performed while the plate is either on or off the bone, by coupling the bending instruments to the drill guides and applying a relative force to bending the tabs about the bridges. A tab may also be easily removed by using the bending tools to reverse bend the tab until a clean fracture of the bridge element is effected.

The medial plate is a low profile plate including a shaft and a relatively enlarged distal head. The shaft includes both threaded fastener holes and compression slots along its length. The most distal slot includes a distal undercut. The head includes preferably seven threaded fastener holes having preferably parallel axes, and preferably arranged in two parallel proximal-distal rows of three and a final hole located along the longitudinal axis of the plate between the two rows. At the distal end of the head, the head includes an extension provided with a non-threaded, non-circular hole.

Each of the plates further includes fixed angle K-wire alignment holes to receive K-wires for provisional fixation of bone fragments and for fluoroscopic confirmation of the location of the plate. K-wires are preferably provided in the system for use with the plates.

A plate holder is also provided which couples to the plates to maneuver the plates subcutaneously through a minimally invasive surgical incision. The plate holder includes a proximal handle, a distal mount, and an arm extending between the handle and the mount. The mount includes a first portion which seats within a slot on the shaft of either plate, and a second portion at which the shaft is coupled and which includes a tapered proximal side. A set screw hole is provided through the first and second portions, and a set screw is provided therein. When the first portion is seated in a compression slot of a plate shaft and the set screw is driven to seat, the set screw locks the mount to the plate shaft. The arm of the plate holder is contoured to seat closely to the head of the plate, but to clear the drill guides in the head portion of the plates. The plate holding tool facilitates percutaneous introduction of the plate, positioning of the plate on the bone surface and holding the plate while holes are drilled through the plate and the first fastener is inserted. A drill sleeve is provided for guiding a bone drill in alignment with the screw holes and drill guides. The drill sleeve includes a cylindrical body having a first end, a second end and a longitudinal axis extending therebetween. The cylindrical body includes a longitudinal bore therethrough that is sized for passage of a bone drill. The drill sleeve also includes a frictional retaining element for exerting a bearing force against the surface of the bone drill, such that the frictional retaining element may support at least the weight of the drill sleeve on the bone drill. The bone drill has graduated indicia, and a portion of the drill sleeve may be referenced relative to the indicia so as to be used as a depth gauge for determining the length of a drilled hole in order to select a screw fastener having the appropriate length.

Each fastener includes a shank portion for engagement into the bone, wherein the shank portion may have one of a cortical thread, a cancellous thread, a non-threaded portion and combinations thereof. The head portion of the fastener may have one of a fixed angle locking head, a non-locking compression head and a multidirectional locking head.

In view of the above, the system facilitates subchondral support of the articular surface so that plate shares the load with bone during healing. The system also facilitates bone targeting and contouring of the plates to the bone so that intra-articular fragments can be captured and fixated, and drilling holes to the proper depth and selection of appropriate length fasteners. The system accomplishes this in a manner that is low profile to minimize soft tissue trauma and patient discomfort and more convenient to the surgeon.

Additional objects and advantages of the invention will become apparent to those skilled in the art upon reference to the detailed description taken in conjunction with the provided figures.

BRIEF DESCRIPTION OF THE DRAWINGS

FIG. 1 is a top perspective view of an anterolateral plate of the distal tibia system of the invention.

FIG. 2 is a bottom perspective view of the anterolateral plate of FIG. 1.

FIG. 3 is a transparent posterior view of the distal tibia with the anterolateral plate of FIG. 1 attached thereto by a plurality of fasteners.

FIG. 4 is a top perspective view of the anterolateral plate of FIG. 1 shown with drill guides attached thereto.

FIG. 7 is a top perspective view of a medial plate of the distal tibia plating system of the invention.

FIG. 8 is a bottom perspective view of the medial plate of FIG. 7.

FIG. 9 is an enlarged top distal perspective distal view of medial plate, shown with drill guides attached thereto.

FIG. 10 is a transparent medial view of the distal tibia with the medial plate of FIG. 7 attached thereto by a plurality of fasteners.

FIG. 11 is a transparent posterior view of the distal tibia with the medial plate of FIG. 7 attached thereto by a plurality of fasteners.

FIG. 14 is a perspective of a plate holder according to the invention.

FIG. 15 is an enlarged distal end broken view of the plate holder of FIG. 14.

FIG. 16 is an anterolateral view of the anterolateral plate and plate holder assembly.

FIG. 17 is a distal perspective view of the assembly of FIG. 16.

DETAILED DESCRIPTION OF THE PREFERRED EMBODIMENTS

Figure 5:
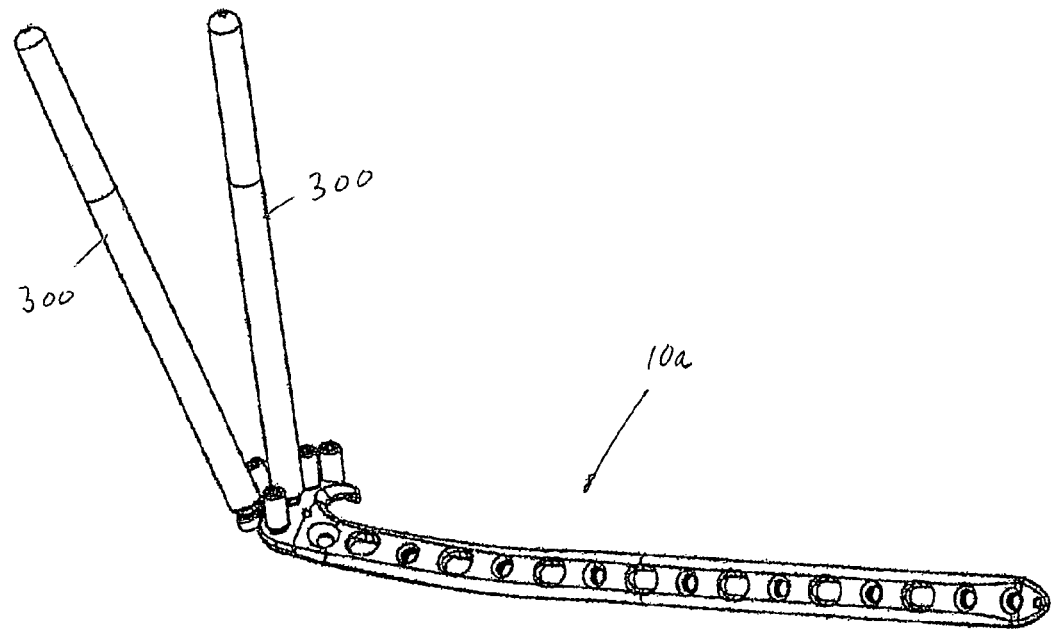
FIG. 5 is a perspective view of another embodiment of an anterolateral plate the distal tibia system of the invention, shown with drill guides and bending tools.

The distal tibia plating system according to the invention includes an anterolateral plate 10 (FIGS. 1-6), a medial plate 110 (FIGS. 7-11), drill guides 200 (FIG. 12-13), bending tools 300 (FIGS. 5-6), a plate holder 400 (FIGS. 14-23), fasteners 500, 600, 700, 800 (FIGS. 24-27), and K-wires, as discussed below.

Anterolateral Plate

Turning now to FIGS. 1 and 2, the anterolateral plate 10 of the distal tibia plating system according to the invention is shown. The anterolateral plate 10 includes a shaft 12 with a longitudinal axis 14, and a distal head 16, and a lower bone contacting surface 18 and an opposite upper surface 20.

The shaft 12 is twisted about the longitudinal axis 14 to match the anterolateral bone surface of the distal tibia. The shaft 12 has a width 22 of between approximately 11 mm-12.2 mm to minimize the profile of the shaft. The shaft 12 has both threaded fastener holes 24 and elongate compression slots 26 longitudinally arranged along its length. The shaft 12 is provided with a preferably alternating arrangement of the threaded fastener holes 24 and slots 26. The number of threaded fastener holes 24 and compression slots 26 is generally dictated by the length of the shaft 12 which can vary depending on the length of the fracture being treated and the stability required. It is preferred that a threaded fastener hole 24 be provided at the proximal end of the plate. At certain plate lengths, this may result in the plate having two consecutive threaded fastener holes 24 at the proximal end (see, e.g., plate 10a in FIG. 5). The threaded fastener holes 24 are preferably triple lead tapered holes, and chamfered at 28 to permit the head of a fastener, described below, to seat lower in the plate 10. The proximal end 30 of the shaft is tapered in width to facilitate percutaneous minimally invasive insertion of the plate.

The distal head 16 widens relative to the shaft 12 to transition into a lateral extension 32. The head 16 is preferably provided in sizes of approximately 33.5 to 38.5 mm in width, depending on anatomical considerations, to provide sufficient support in a minimized profile. The lower surface 18 of the head 16 is preferably curved in the medial-lateral direction to wrap around the distal tibia. The head 16 includes a non-threaded compression screw hole 34 and a first row of preferably four threaded fastener holes 36 having the same thread structure as holes 24. A plurality of distal tabs 38 (preferably two or three tabs) are coupled to the distal head. Each tab has a threaded hole 40 with the same thread structure as holes 24 and 36. Holes 40 are together aligned to define a second row of threaded fastener holes. The first and second rows of threaded holes 36, 40 are approximately parallel and the threaded holes 40 of the second row are staggered (transverse to the longitudinal axis 14) with respect to the threaded holes 36 of the first row. The axial arrangement of the first and second rows is such that thread axes 42 through the threaded holes of the second row converge in a proximal-distal direction below the bone contacting surface 18 of the plate relative to the thread axes 44 through the threaded holes of the first row, and that such thread axes 42 through the second row pass between the thread axes 44 through the first row. Referring to FIG. 3, this arrangement of thread axes allows fasteners 500 (generally, but any of the fixed angle fasteners discussed herein) inserted along the thread axes 42, 44 to form a load-bearing scaffold to support the articular surface 46 of the distal tibia 48 against the talus of the foot. The threaded holes in the first row are preferably chamfered so that the head 502 of fasteners 500 can seat low in the plate 10. As discussed further below, the tabs 38 are of a thinner construction than the remainder of the head 16 of the plate. The threaded holes 40 in the tabs 38 are preferably not chamfered so that the tabs have sufficient structural support to engage a selected fastener.

Figure 6:
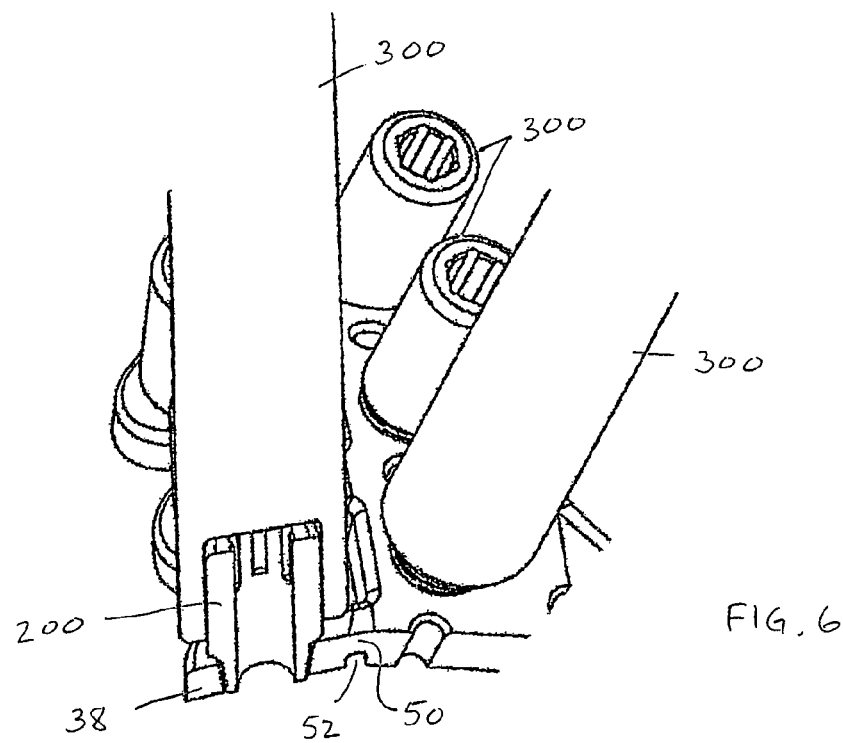
FIG. 6 is an enlarged section view illustrating the structure of the distal head of the anterolateral plate and the attachment of the bending tools to the guides.

Referring to FIG. 4, each of the threaded fastener holes can be provided with a pre-assembled drill guide 200, described in more detail below with respect to FIGS. 12 and 13, that is adapted to guide a drill into bone in axial alignment with the fastener hole. Referring to FIGS. 5 and 6, each drill guides 200 is adapted to couple relative to one member of a pair of bending tools 300 to re-orient the configuration of the tabs by the surgeon, also described in more detail below. It is preferable that each such fastener hole 40 in the second row be provided with a drill guide 200, and that the other fastener holes optionally be provided with such drill guides.

Referring to FIGS. 1-3 and 6, each distal tab 38 is ring-shaped and is connected to the distal end of the head 16 of the plate 10 with a bridge 50. The tabs 38 are preferentially bendable to customize the load bearing support of the articular surface 46 of the distal tibia 48. The bridge 50 of each tab 38 is configured to bend preferentially in rotation about the y-axis. To that end, each bridge 50 preferably has a rectangular cross-section, with width greater than thickness. In addition, the bridges may include a lower recess 52 in the width-wise direction. Then if bent, the new thread axis 42 of a fastener hole 40 will not intersect the thread axis 44 of a threaded fastener hole 36 of the first row in the head portion. To effect bending, the bending tools 300 are fit over (as shown) or into two adjacent drill guides 200, one located in a tab 38 and one located in a thread hole 36 of the first row. Force is applied to the proximal ends of the bending tools 300 to effect bending of the tab 38 relative to the head portion 16 of the plate 10. Thus, one or more of the tabs 38 can be easily reconfigured relative to the of the plate, e.g., to capture the distal rim of the tibia, to capture a specific bone fragment or buttress and support a desired area. Tab bending may easily be effected while the plate is on the bone. Further, by designing the area of the tab 38 around the fastener hole 40 thicker than the bridge 50, it is ensured that the hole 40 and threads thereof are not deformed when bending a tab 38 to a desired orientation. Moreover, the lower recess 52 also facilitates removing a tab 50 with the bending tools 300 by reverse bending the tab 38 until a clean fracture of the bridge 50 is effected. The tabs 38 are purposefully designed to fracture upon application of 20-25 in-lb force, i.e., by bending each of tabs 38 down about 30 degrees and back up about 30 degrees.

The anterolateral plate includes K-wire alignment holes 56, 58, 60 that receive K-wires for provisional fixation of bone fragments and for fluoroscopic confirmation of the location of the plate. First alignment holes 56 are preferably provided in the head portion of the plate between the threaded holes 38 of the first row, a second alignment hole 58 is provided between the first row of threaded holes 38 and the compression hole 34, and a third alignment holes 60 is provided at the proximal end 30 of the plate 10. Each K-wire alignment hole preferably provides fixed angle alignment to a K-wire inserted therethrough. K-wires (not shown) are preferably provided with the system for use with the anterolateral plate 10, as well as the medial plate 110, discussed below.

Medial Plate

Referring to FIGS. 7 through 9, the medial plate 110 includes a shaft 112 with a longitudinal axis 114 and a relatively broader distal head 116. The shaft 112 has a shallow radius of curvature transverse to the longitudinal axis. This shallow radius enable the shaft to have a thickness that is approximately 25 percent thinner than competitive plates. The shaft 112 includes an arrangement of both threaded fastener holes 124 and compression slots 126, along its length, similar to the anterolateral plate 10. The threaded fastener holes 124 are preferably triple lead tapered thread holes. The proximal end 130 of the plate may include consecutive threaded fastener holes. The most distal slot 128a includes a peripheral undercut 133a, discussed in more detail below.

The head 116 of the plate 110 includes preferably seven threaded fastener holes 136 having the same hole and thread structure as holes 124. The holes 136 preferably parallel axes, and preferably arranged in two substantially parallel proximal-distal rows 135, 137 of three and a central hole 136a located between the two rows. At the distal end of the head, an extension 139 is provided with a non-threaded, non-circular hole 141 which can be used to direct a compression screw along axis 143 towards the thread axis 145 of the central hole 136a (FIG. 11). Each of the threaded holes is preferably of the same size and structure as the threaded holes in the anterolateral plate 10. In addition, each of the threaded holes in at least the head 116 is preferably provided with a drill guide 200 for guiding a drill. The drill guide 200 is described in more detail below with respect to FIGS. 12 and 13.

A first K-wire alignment hole 156 is provided between the central hole 136a and the non-circular hole 141 and a second K-wire alignment hole 160 is provided at the proximal end 130 of the shaft 112 to facilitate alignment and temporary positioning of the plate on the bone. FIGS. 10 and 11 show the medial plate implanted on the medial side 160 of the distal tibia 48.

Each of the plates 10, 110 of the present system may be formed from any one of numerous materials known in the art, including a stainless steel, a titanium and a titanium alloy such as Ti-6Al-4V. More preferably, each of the plates is preferably machined from a solid round bar of Ti-6Al-4V-ELI in the fully annealed condition. Each plate is machined to its respective anatomical shape to ensure minimal work hardening. After machining, the parts are polished and anodized. The resulting plate material is fully 'soft' and permits the ability to bend the plate at the tabs or relative to the longitudinal axis without fracture of the plate. In general, each of the plates described herein is significantly thinner than currently available plates for the same types of fractures, yet still has the appropriate rigidity for internal fixation of the fractured bone.

Drill Guides

Figure 12:
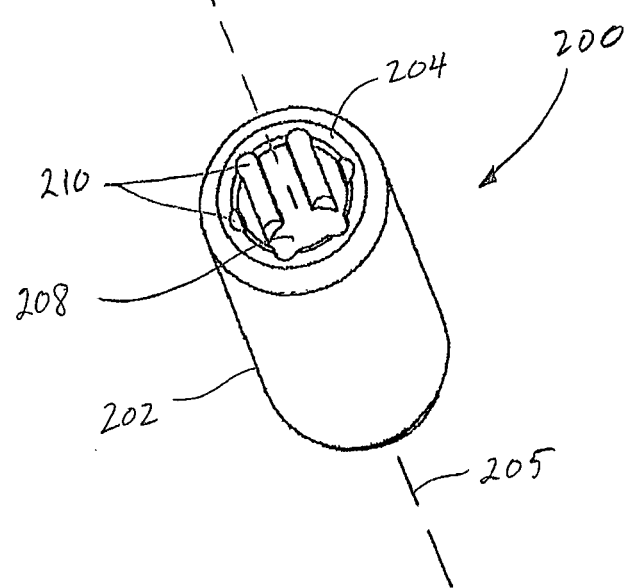
FIG. 12 is a top perspective view of drill guide for use with the distal tibia plating system of the invention.
Figure 13:
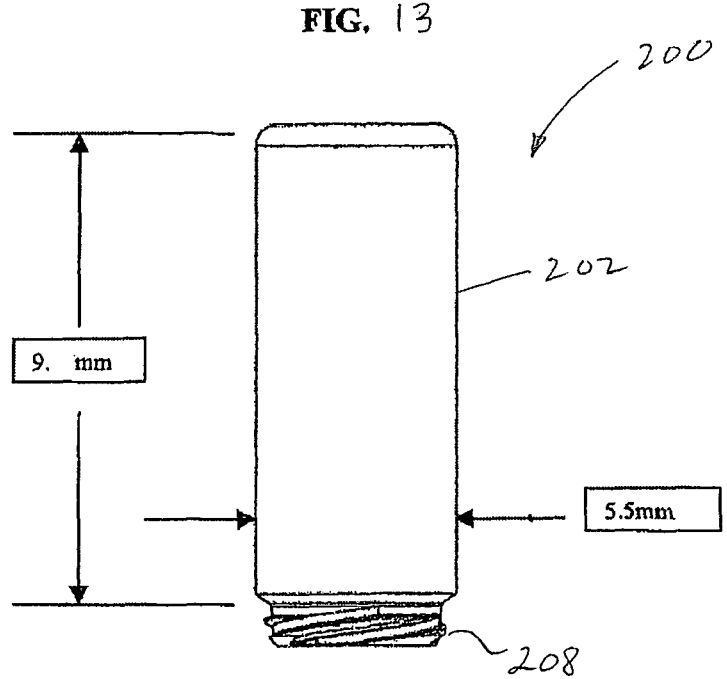
FIG. 13 is a side elevation of the drill of FIG. 12.
Figure 18:
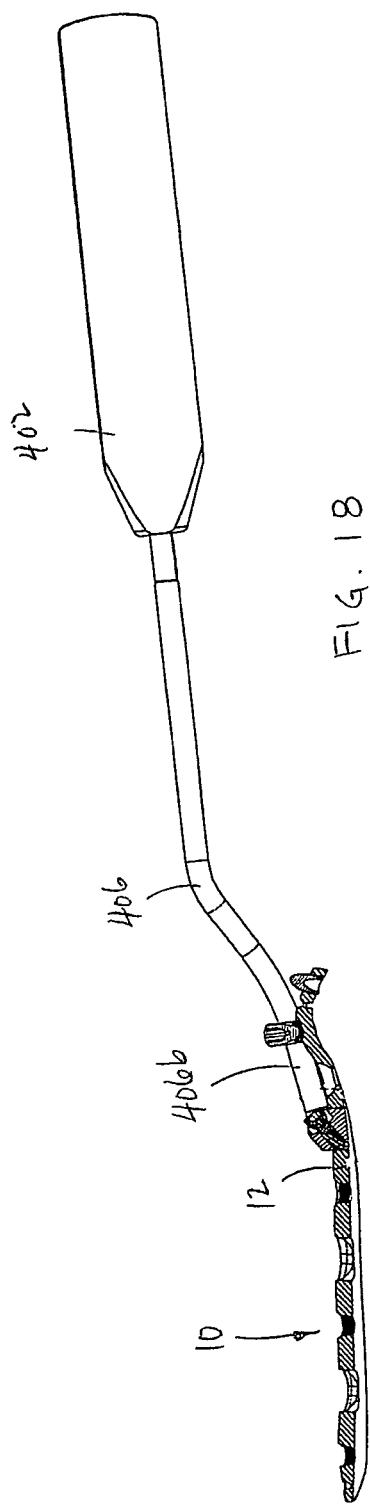
FIG. 18 is section view through the longitudinal axis of the anterolateral plate of the assembly of FIG. 16.
Figure 19:
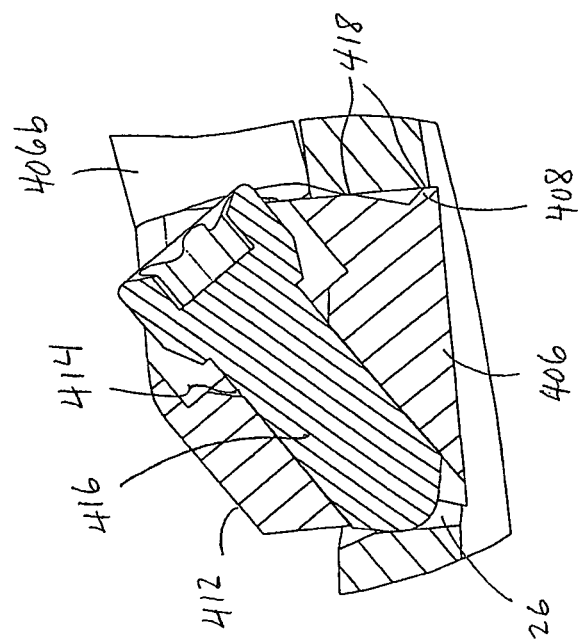
FIG. 19 is an enlarged section view through the coupling of the plate holder to the anterolateral plate.
Figure 20:
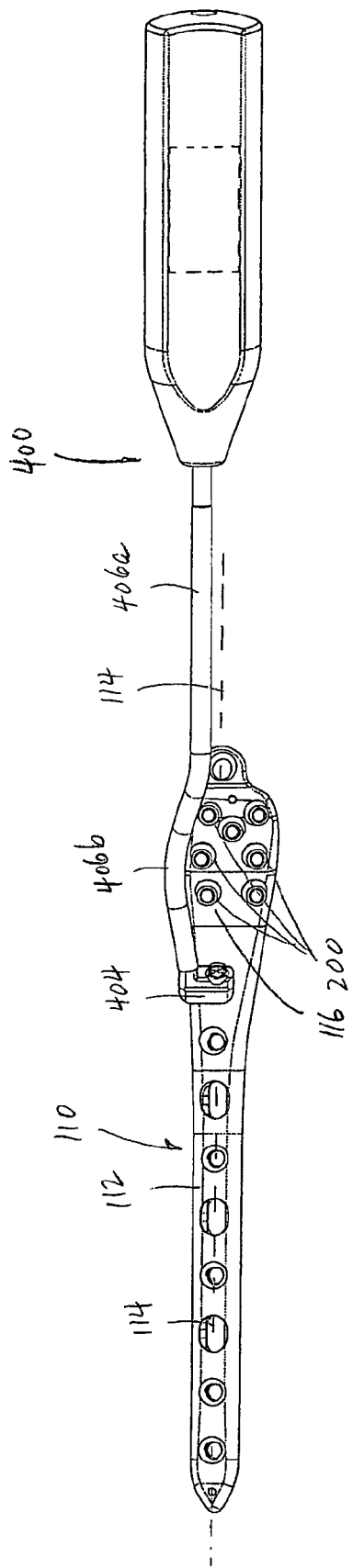
FIG. 20 is a medial view of the medial plate and plate holder assembly.
Figure 21:
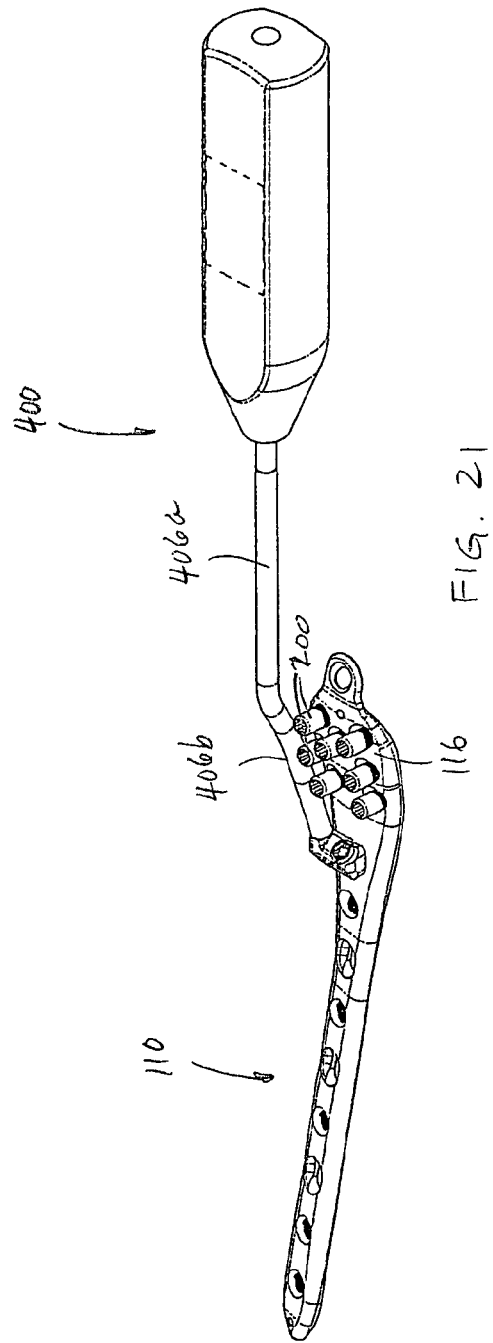
FIG. 21 is a distal perspective view of the assembly of FIG. 20.
Figure 22:
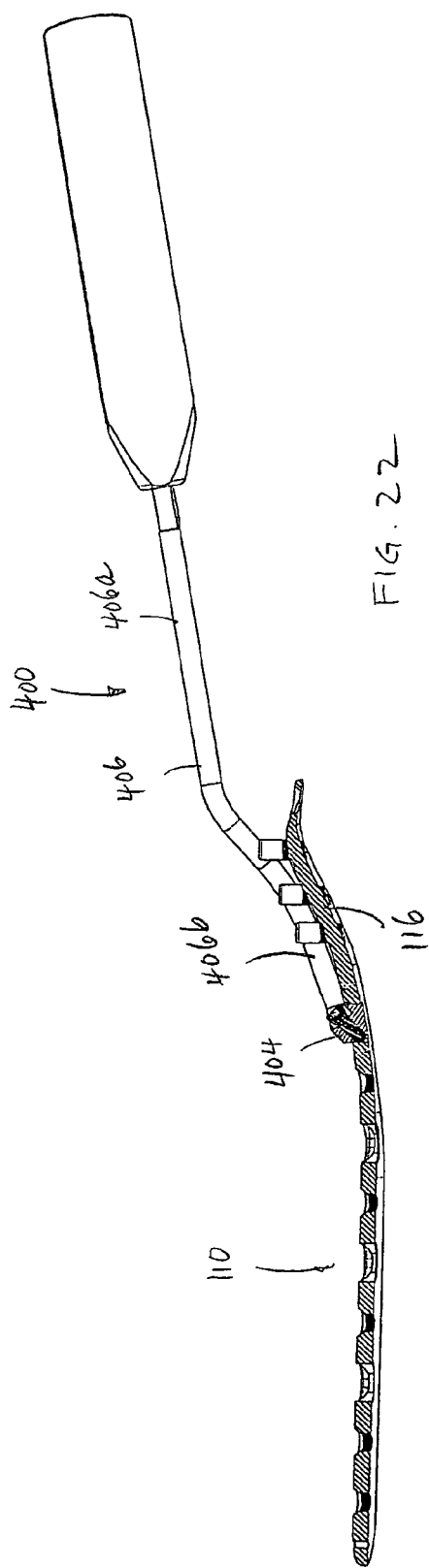
FIG. 22 is section view through the longitudinal axis of the medial plate of the assembly of FIG. 20.
Figure 23:
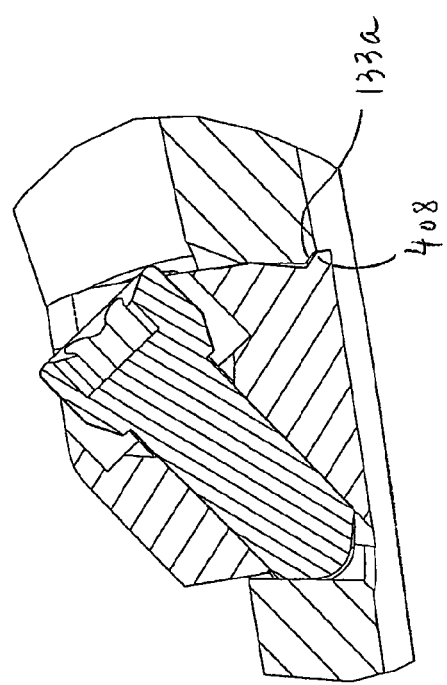
FIG. 23 is an enlarged section view through the coupling of the plate holder to the medial plate.

Referring to FIGS. 12 and 13, a drill guide 200 having a cylindrical body 202, a proximal end 204, and a distal end 206 is shown. The drill guide 200 also has an axis 205 and a longitudinal bore 208 sized for guiding a conventional bone drill. A plurality of internal drive elements 210 are formed in bore 208 near proximal end 204. In this embodiment, the plurality of internal drive elements 210 include six internal drive elements 210 for receiving the hexagonally shaped distal tip of a conventional bone screw driver tool, although other configurations and quantities of internal drive elements 210 are possible.

The distal end 208 of the drill guide 200 is provided with a tapered threaded portion 212 configured for threaded engagement with a tapered threaded hole of both the anterolateral or medial bone plates, such that axis 205 is colinear with the axis of the tapered threaded hole.

The cylindrical body 202 preferably has a length of approximately 9 mm from the proximal until the start of the threaded portion 212, and an external diameter of approximately 5 mm.

The bone plates 10, 110 may be provided to the surgeon with each tapered threaded hole of the bone plate already preassembled with drill guide (or guides preassembled in selected threaded holes), so that it is not necessary for the surgeon or an assistant to attach a drill guide to each hole during the procedure as is normally done for conventional bone plating systems. In this way, the surgeon may quickly drill several bone holes, such that the axis of each hole is in perfect alignment with the hole thread axis. The surgeon may then remove the drill guide using the hexagonally tipped driver and insert a locking bone fastener, such that the threaded head of the locking fastener easily engages with the threaded hole. The pre-assembly of a drill guide to a bone plate is described in co-owned U.S. Pub. No. 20060149250A1, and the use of such drill guide for bending a plate is described in co-owned U.S. Pub. No. 20060161158A1, 20070233111A1, and 20070233112A1, all of which are hereby incorporated by reference herein in their entireties.

The drill guides are preferably color coded, so to provide a visual cue to the surgeon and staff as to whether a plate is for the left or right bone. For example, guides may be color green for left application and red for right application.

Plate Holder

Referring to FIGS. 14 and 15, a plate holder 400 is also provided which can be coupled to the plates 10, 110 to maneuver the plates subcutaneously through a minimally invasive surgical incision. The plate holder 400 includes a handle 402, a mount 404, and an arm 406 extending between the handle 402 and the mount 404. The mount 404 includes a first portion 406 with a lip 408 which seats within a distalmost compression slot on the shaft of either plate, and a second portion 410 at which the arm is permanently secured. The second portion 410 includes a tapered proximal side 412 to ease insertion under soft tissue. A set screw hole 414 is provided through the first and second portions, and a set screw 416 is provided therein. When the first portion 406 is seated in a slot of a plate shaft and the set screw 416 is driven to seat, the set screw drivers the first portion 406 into compression with the plate shaft to lock the holder 400 and plate into an assembly. The arm 406 of the plate holder 400 is contoured to seat closely to the head of the respective plate, but to clear the drill guides 200 in the head portion of the plates. The plate holder facilitates positioning of the plate on the bone surface and holding the plate while the first fastener is inserted.

More particularly, referring to FIGS. 16 through 19, the plate holder 400 is shown coupled to the anterolateral plate 10. In the anterior view, the proximal portion 406a of the arm 406 (adjacent the handle) of the holder 400 extends in the same plane as the longitudinal axis 14 of the shaft 12 of the plate 10. The distal portion 406b of the arm (adjacent the plate) is contoured about the head so as to not interfere with the drill guides 200 but to extend close to the plate (see vertical dimension in FIG. 18) to limit interference with soft tissue during plate insertion. When the mount 404 is coupled relative to the plate, the lip 408 does not extend under the compression slot 26 of the plate 10. The set screw 416 forces a distal wall 418 of the first portion 406 against a wall of the slot to engage the holder 400 relative to the plate. The holder 400 may be released from the plate by loosening the set screw. The angle of the set screw hole 414 and set screw 416 is approximately 35° so as to effect appropriate compression and be easily accessed via a driver even once the plate is at the implantation site.

Referring to FIGS. 20 through 23, the same plate holder 400 is shown attached to the medial plate 110. The proximal end 406a of the arm 406 is also in-plane with the shaft axis 114, and the distal end 406b is contoured about the head 116 so as to not interfere with drill guides 200 and to maintain a low profile to the plate. The distal compression slot 126a of the medial plate includes an undercut 133a. When the first portion of the mount is inserted into the slot 126a, the lip 408 engages at the undercut 133a to further secure the holder to the plate 110.

Plate holders 400 may be color coded for left and right plates (e.g., green-left; right-right) and correspond in color to the drill guides to facilitate engagement to the correct plate.

Drill Sleeve

Figure 28:
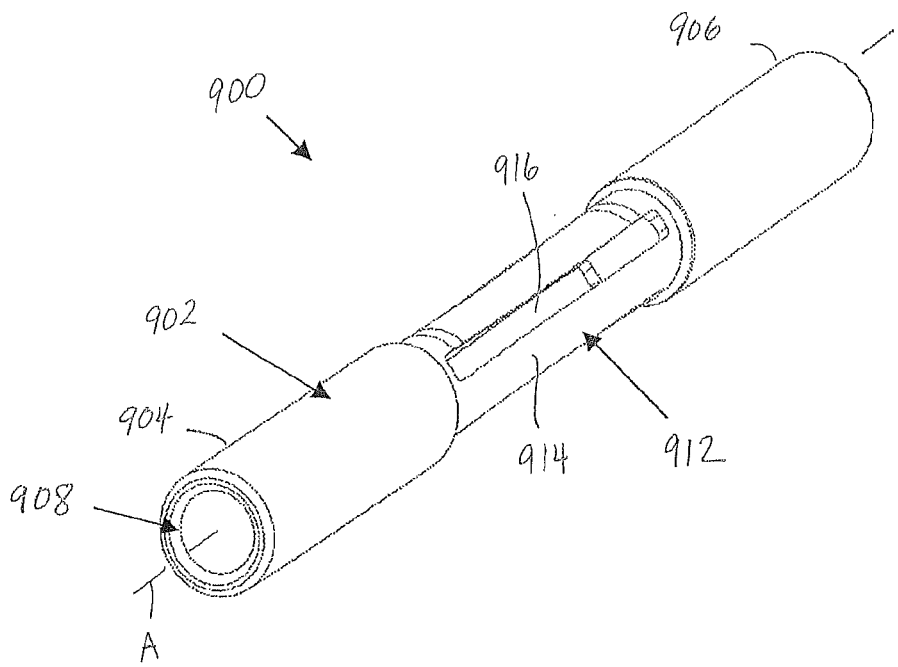
FIG. 28 is a perspective view of a drill sleeve according to the invention.
Figure 29:
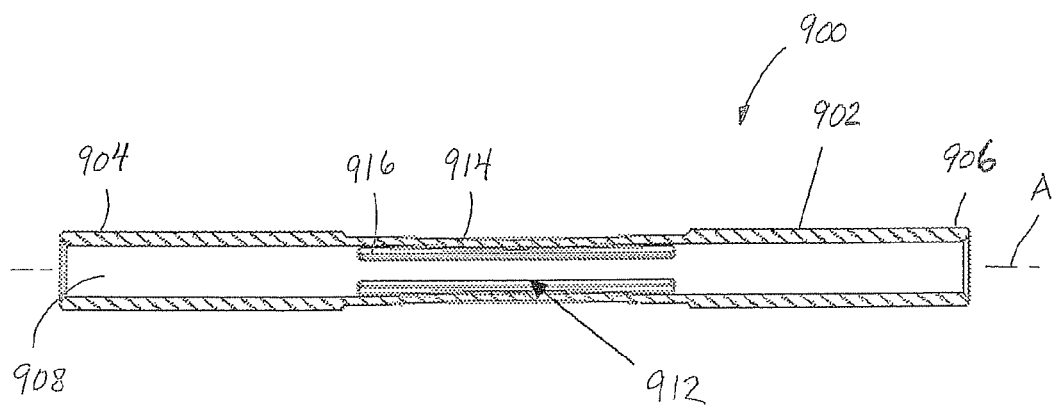
FIG. 29 is a sectional view of the drill sleeve of FIG. 28.
Figure 30:
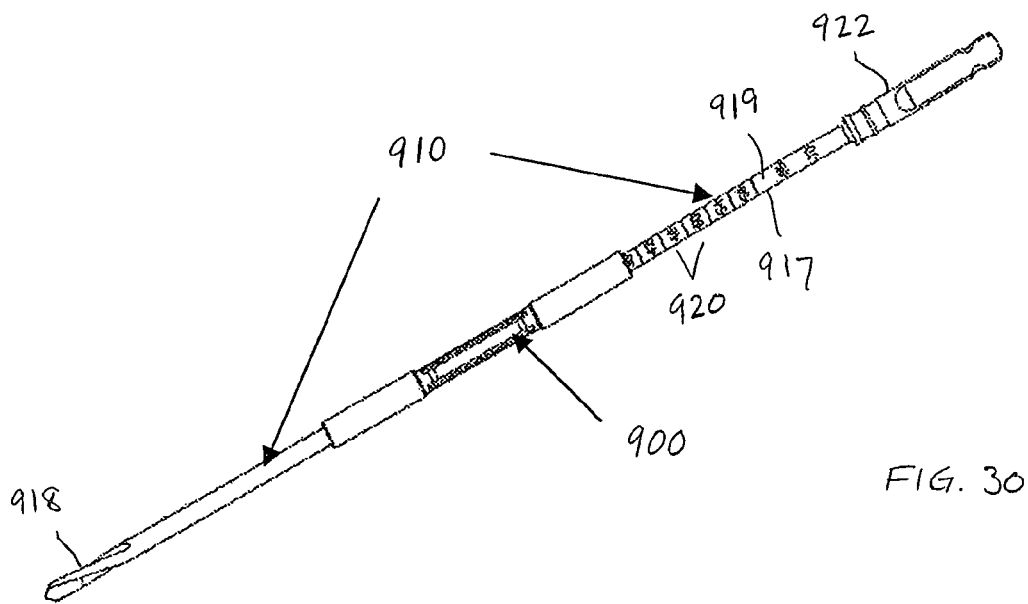
FIG. 30 is a side view of a drill sleeve positioned and frictionally retained on a bone drill.
Figure 31:
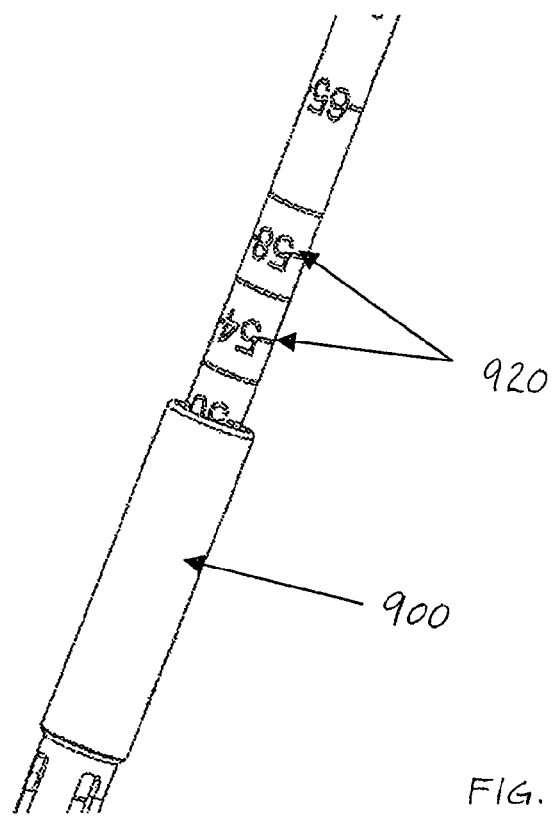
FIG. 31 is a detailed view of the drill sleeve and drill of FIG. 30, showing drill indicia for determining the required bone screw length.
Figure 32:
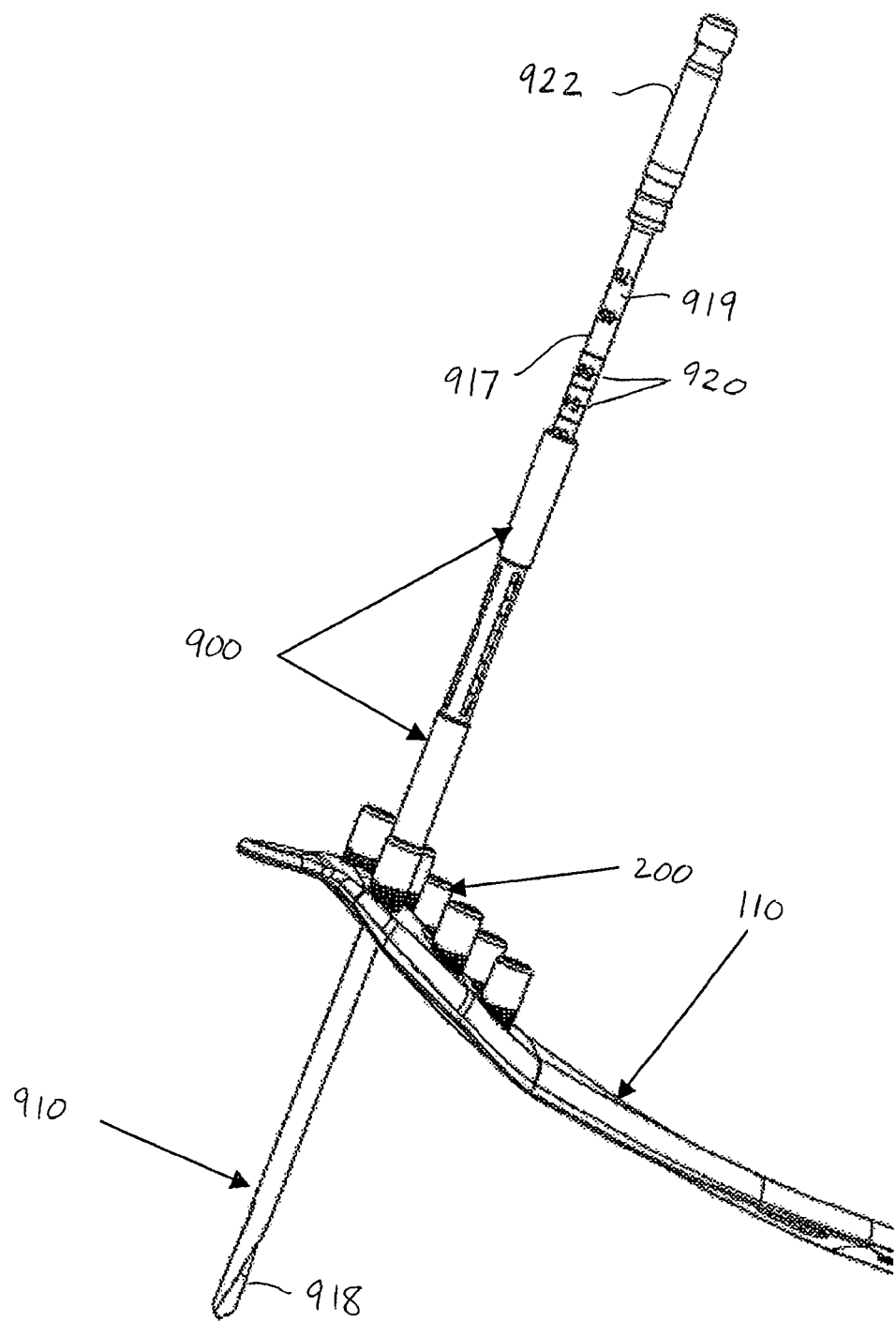
FIG. 32 is a perspective view of the drill sleeve and drill of FIG. 30, shown as it may be inserted into a drill guide that is preassembled to a bone plate.

Turning now to FIGS. 28 through 32, a system is also provided for determining the depth a hole drilled with a bone drill. Referring specifically to FIGS. 28 and 29, the system includes a drill sleeve 900 having a cylindrical body 902 with a first end 904, a second end 906, and a longitudinal axis A extending therebetween. The cylindrical body 902 includes a longitudinal bore 908 therethrough that is sized for passage of a bone drill 910 (FIGS. 30-32). The drill sleeve 900 also includes a frictional retaining element 912 for exerting a bearing force against the surface of the bone drill 910, such that the frictional retaining element 912 may support at least the weight of the drill sleeve 900 on the bone drill 910. This permits the sleeve 900 to holds its longitudinal position on the bone drill 910 in the absence of other significant external forces. However, the bearing force is small enough to allow longitudinal translation of the drill 910 through the bore 908 when the sleeve 900 is longitudinally held relatively to the bone and the drill is advanced into the bone during normal use. In addition, the bearing force is small enough to allow normal rotation of the drill 910 in the bore 908 when the drill sleeve is held, such as by the user's fingers.

The frictional retaining element 912 may have four parallel, longitudinal spring elements 914 evenly spaced around the periphery and in the middle portion of the cylindrical body 902. These spring elements 914 may be formed, for example, by milling four longitudinal windows 916 in the wall of the cylindrical body. At least one of the spring elements 914, and preferably a pair of opposing spring elements, may be bent or crimped radially inward to slightly intrude into the volume defined by the bore 908.

According to the embodiment of the drill sleeve shown in the figures, the drill sleeve 900 may have a round, elongate, cylindrical shape, such that when used with the drill 910, the drill sleeve 900 does not significantly limit access or visibility within the wound site. The drill sleeve 900 may be formed from a stainless steel and treated by a well-known, titanium nitride coating process, primarily to increase the surface hardness to prevent significant wear of the inside surface of the bore. Other materials, including metals and plastics can also be used. To accommodate the various sizes of bone drills, the drill sleeve may be provided with any one of a plurality of bore diameters.

As shown in FIGS. 30 through 32, the drill sleeve may be used with a bone drill 910. The bone drill 910 includes a shaft 917 with a boring end 918, an opposite tool engaging end 922, a surface 919, and graduated indicia 920 provided on the surface. A surgeon may use the drill sleeve 900 and bone drill 910 in combination as a depth gauge to measure the depth of a hole drilled into a bone in order to select a bone screw having the appropriate length. For the embodiment shown in FIG. 32, the length of the drill sleeve 900 and/or the indicia 920 on the bone drill 900 takes into account the thickness of the bone plate 110 and the length of the drill guide 200 that is preassembled to the plate. The drill sleeve 900 is preferably longitudinally symmetric so that it may be assembled onto the bone drill 910 such that either one of the first and second ends 902, 904 is distal to the user, and that it does not matter into which end of the drill sleeve 900 that the drill 910 is inserted.

Referring to FIG. 32, in use, the drill 910 is inserted into the drill sleeve 900 prior to insertion into the drill guide 200 and bone plate 110. Then, after the bone plate 110 is positioned on the bone, the drill is directed by the axis of the drill guide 200 into proper orientation for the respective hole. As the hole is drilled into the bone, the drill sleeve 900 identifies the indicia 920 to be referenced up and out of the wound so that it is more readable to the surgeon. However, it should is recognized that a powered drill is coupled at the tool engaging end 922 of the drill. Therefore, rather than bend over and try to view the indicia 920 referenced on the drill at the top of the drill sleeve 900 and below the powered drill while the bone drill 910 is located through the plate 110 and in the bone, the surgeon can remove the bone drill 910 from the bone and see the same information without leaning over the wound and without losing the reference of the top of the sleeve relative to the indicia on the drill. As indicated above, the retaining element 912 operates to maintain the longitudinal position of the drill sleeve 900 on the bone drill 910 even after it is removed from the bone, plate 110 and drill guide 200. After the depth of hole is read from the indicia 920, if necessary, the bone drill (with or without sleeve) can be returned to the hole for further drilling.

The drill sleeve 900 may be permitted to rotate together with the drill 910 during usage. However, normally when the drill sleeve 900 is held against the drill guide 200 as shown in FIG. 32, there is sufficient friction between the sleeve 900 and the guide 200 to prevent the sleeve from rotating as fast as the drill 910, if at all. In any case, rotation of the drill sleeve while drilling does not affect the ability to use the sleeve/guide combination as a depth gauge.

Using the drill sleeve and the drill with indicia in combination as a depth gauge eliminates the step of using a feeler probe and gauge to determine required bone screw length.

In addition to the above advantages, the drill sleeve is of relatively simple manufacture and can therefore be made at low cost. Therefore, the materials used can be adapted for one-time disposable use or given its construction, it can be easily cleaned and sterilized for reuse. Moreover, it is easy to use, intuitive, and requires very little learning curve. As such, its use and benefit can be readily implemented in the field.

Fasteners

Each of the threaded holes in both plates 10, 110, whether in the head or shaft portions of the anterolateral or medial plate can all receive the same fastener types. Thus, the fasteners in the system are interchangeable between the plates. Generally, the fasteners includes a shank portion for engagement into the bone, wherein the shank portion may have one of a cortical thread, a cancellous thread, a non-threaded portion and combinations thereof. Each fastener type further includes a head portion for engagement with the fastener hole, wherein the head portion may have one of a fixed angle locking head, a non-locking compression head and a multi-directional locking head.

Figure 24:
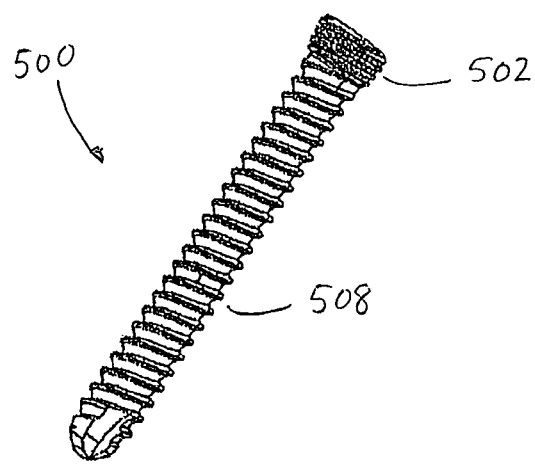
FIG. 24 is side elevation view of a fixed angle locking cortical screw for use with the bone plates of the distal tibia system of the invention.
Figure 25:
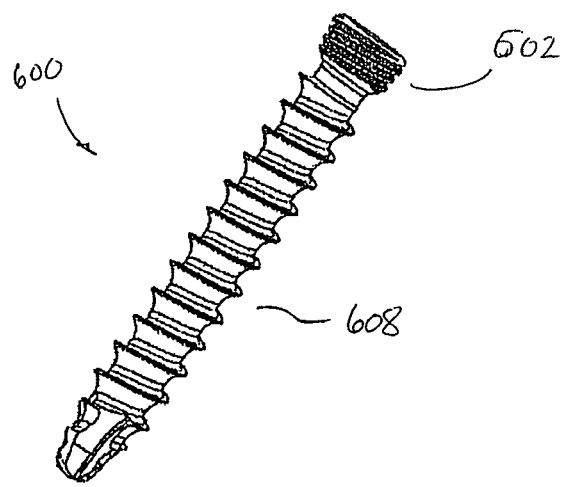
FIG. 25 is side elevation view of a fixed angle locking cancellous screw for use with the bone plates of the distal tibia system of the invention.

FIGS. 24 through 27 show four embodiments of fixed angle bone fasteners. FIG. 24 is a side view of a fixed angle locking screw 500, which includes a tapered threaded head 502 having a driver recess (not shown), and a threaded shaft 504. The threads on the shaft having a pitch adapted for engaging cortical bone. Screw 500 may be inserted and locked into a tapered, threaded hole of a bone plate at a fixed angle predetermined by the hole thread axis. FIG. 25 is a side view of a fixed angle locking screw 600, substantially similar to screw 500, but wherein the threads of shaft 604 have a relatively larger pitch adapted for engaging cancellous bone.

Figure 26:
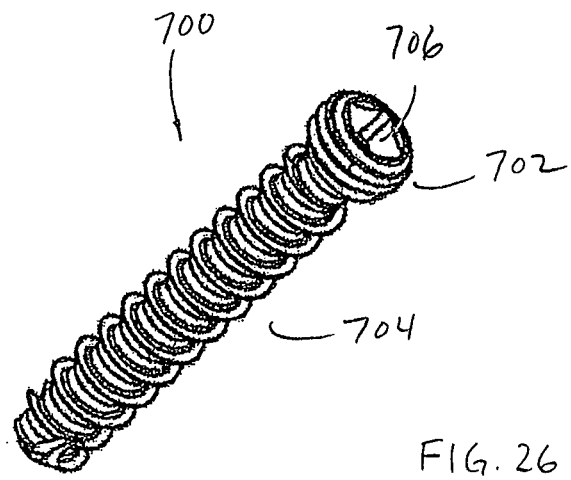
FIG. 26 is perspective view of a multidirectional locking screw for use with the bone plates of the distal tibia system of the invention.

FIG. 26 is a side view of a multidirectional locking screw 700. Screw 700 includes a head 702 with a square drive recess 706, and a shaft 704. The screw 700 may be locked into either plate, such that a screw axis forms an angle in the range of 0-15 degrees with the thread axis of the hole. Screw 700 may be formed from a cobalt-chrome alloy that is significantly harder than the plate material, which may be a titanium alloy. Such a multidirectional locking screw is described in detail in U.S. Pub. No. 20070088360A1, which is hereby incorporated by reference herein in its entirety.

For the fastener embodiments 500, 600, and 700, the shaft alternatively be smooth along all or a portion of its length.

Figure 27:
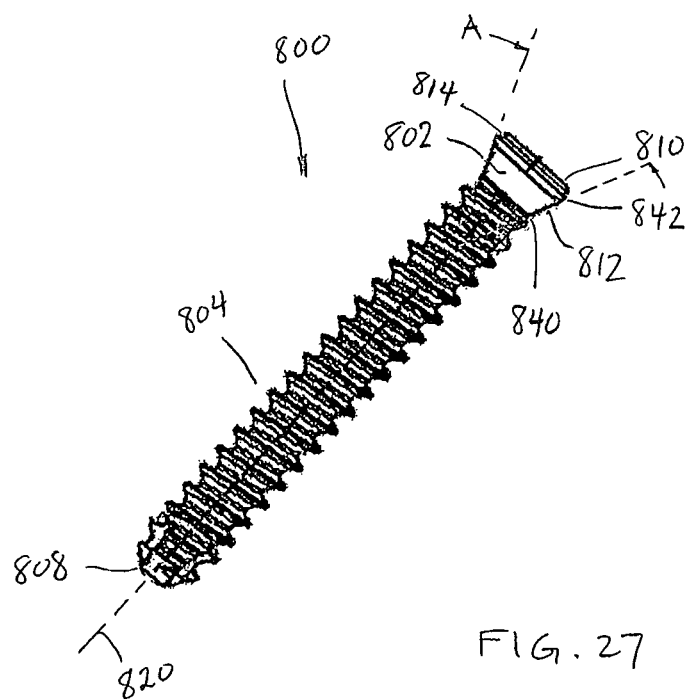
FIG. 27 is side elevation view of a multidirectional compression fastener for use with the bone plates of the distal tibia system of the invention.

FIG. 27 is a multidirectional compression fastener 800, also called screw 800. Screw 800 includes a threaded shaft 804 and a distal tip 808. Screw 800 further includes a head 802 having a proximal face 810 with a square drive recess, although other drive recess configurations are possible. Head 802 includes a smooth, frustoconical portion 812 having a small diameter end 840 attached to body 804 and a large diameter end 842 forming a peripheral edge 814 of proximal face 810. Frustoconical portion 812 has an included angle (indicated by A) centered on a screw axis 820. Peripheral edge 814 may have an external radius. Threads of screw shaft 804 may be either cancellous or cortical, and may optionally be formed along only a portion of the length of the shaft 804.

As will be appreciated by those skilled in the art, the present system described herein provides to a surgeon the advantageous option to use any one of a standard compression screw (no shown, but for use through non threaded holes), a fixed angle locking screw (screws 500, 600), a multidirectional locking screw (screw 700), or a multidirectional compression screw (screw 800) in the same tapered threaded hole, which is included in both of the bone plates described herein. In addition, each of screws 600, 600, 700, 800 is insertable into the tapered threaded hole, such that the screw head is minimally proud relative to the top surface of the bone plate, thereby minimizing patient discomfort and complications due to soft tissue irritation.

In view of the above, the system facilitates diaphyseal, metaphyseal, and subchondral support of the articular surface of the distal tibia so that plate shares the load with bone during healing. The system also facilitates bone targeting and contouring of the plates to the bone so that intra-articular fragments can be captured and fixated. The system accomplishes this in a manner that is low profile to minimize soft tissue trauma and patient discomfort.

There have been described and illustrated herein several embodiments of plates of a distal tibia plating system. While particular embodiments of the invention have been described, it is not intended that the invention be limited thereto, as it is intended that the invention be as broad in scope as the art will allow and that the specification be read likewise. Where the terms 'approximate', 'approximately' or 'substantially' are used herein, such terms are to be defined as ±20 percent of a given number, amount, or relative position or location, as determined by context. It will therefore be appreciated by those skilled in the art that yet other modifications could be made to the provided invention without deviating from its spirit and scope as claimed.

What is claimed is:

1. A gauge system, comprising:
a) a bone drill having a shaft with a boring end, an opposite tool engaging end, a surface, and graduated indicia provided on said surface; and
b) a drill sleeve having a one-piece cylindrical body with a first end, a second end, a longitudinal axis extending therebetween, and a longitudinal bore extending along the longitudinal axis sized for passage of the bone drill, said drill sleeve being longitudinally symmetrical such that said first end is structurally identical to said second end, and a frictional retaining element integrally formed with said cylindrical body for exerting a bearing force against said surface of the bone drill, said frictional retaining element includes at least one spring element that intrudes inwardly into a volume defined by said bore,
said drill sleeve having a weight and said bearing force of said frictional retaining element being sufficiently large to support at least the weight of said drill sleeve on said bone drill so as to hold a longitudinal position of said drill sleeve on said bone drill, and said bearing force being sufficiently small to allow longitudinal translation of said drill through said bore when said drill sleeve is held stationary,
wherein a depth of a hole drilled by said bone drill is determined by referencing a location of said drill sleeve relative to said indicia on said bone drill, and given said longitudinal symmetry of said drill sleeve said depth is determinable regardless of whether said first end or said second end of said drill sleeve is advanced first over said bone drill.

2. A gauge system according to claim 1, wherein:
said bearing force of said frictional retaining element is sufficiently small to allow rotation of the drill in said bore when said drill sleeve is held stationary.

3. A gauge system according to claim 1, wherein:
said frictional retaining element includes a plurality of spring elements spaced about a periphery of said bore and in contact with said surface of said drill.

4. A gauge system according to claim 3, wherein:
said plurality of spring elements are positioned in a middle portion of said cylindrical body.

5. A gauge system according to claim 1, further comprising:
a bone plate having a thickness and a screw hole extending through said plate in a direction of said thickness; and
a drill guide having a cylindrical bore, a distal end fixed in said hole, and a proximal end, said drill guide having a length extending from said plate to said proximal end,
wherein said drill sleeve is seated on said proximal end of said drill guide.

6. A gauge system according to claim 5, wherein:
wherein said indicia of said depth of said hole drilled by said bone drill is offset along said bone drill by a distance corresponding relative to said thickness of said plate, said length of said drill guide, and said length of said drill sleeve.

7. A gauge system according to claim 5, wherein:
said screw hole in said plate is threaded, said distal end of said drill guide is threaded, and said distal end of said drill guide is threadedly mated to said screw hole.

8. A gauge system according to claim 5, wherein:
said proximal end of said drill guide includes a torque driver mating structure.

9. A gauge system according to claim 5, wherein:
said length of said drill guide is 9 mm, and said drill guide has a diameter of 5 mm.

10. A gauge system according to claim 6, wherein:
when said drill sleeve is seated on said proximal end of said drill guide so that said drill sleeve is in a position relative to said drill guide for referencing said depth of said hole drilled by said bone drill, said drill guide and said drill sleeve are matingly disengaged.

11. A gauge system according to claim 1, wherein:
said drill sleeve has a length, and said length is divisible into first and second halves, and said drill sleeve along said first half of said length is structurally identical to said drill sleeve along said second half of said length.

12. A gauge system according to claim 1, wherein:
said frictional retaining element includes a spring radially displaced into said longitudinal bore, said cylindrical body has a length extending between said first and second ends, and said spring is located at a midpoint of said length.

13. A gauge system, comprising:
a) a bone drill having a shaft with a boring end, an opposite tool engaging end, a surface, and graduated indicia provided on said surface; and
b) a drill sleeve having a cylindrical body with a first end, a second end, a longitudinal axis extending therebetween, a longitudinal bore extending along said longitudinal axis sized for passage of the bone drill, a length extending along said longitudinal axis, said length divisible into first and second halves, said drill sleeve along said first half of said length structurally identical to said drill sleeve along said second half of said length, and a frictional retaining element integrally formed with said cylindrical body between said first and second ends for exerting a bearing force against said surface of the bone drill, said frictional retaining element include a plurality of spring elements, said first and second halves of said cylindrical body meet at a middle portion of said cylindrical body, and said plurality of spring elements of said frictional retaining element are positioned at said middle portion,
said drill sleeve having a weight and said bearing force of said frictional retaining element being sufficiently large to support at least the weight of said drill sleeve on said bone drill so as to hold a longitudinal position of said drill sleeve on said bone drill, and said bearing force being sufficiently small to allow longitudinal translation of said drill through said bore when said drill sleeve is held stationary.

14. A gauge system according to claim 13, wherein:
a depth of a hole drilled by said bone drill is determined by referencing a location of said drill sleeve relative to said indicia on said bone drill.

15. A gauge system according to claim 14, wherein:
said depth is determined by referencing one of said first and second ends relative to said indicia on said bone drill.

16. A gauge system according to claim 13, wherein:
said cylindrical body and said frictional retaining element of said gauge are together manufactured from one-piece of material.

17. A gauge system, comprising:
a) a bone drill having a shaft with a boring end, an opposite tool engaging end, a surface, and graduated indicia provided on said surface; and
b) a drill sleeve having a body with a first end, a second end, a longitudinal axis extending therebetween, a longitudinal bore extending along said longitudinal axis sized for passage of the bone drill, a length extending along said longitudinal axis, said length divisible into first and second halves, said drill sleeve along said first half of said length structurally identical to said drill sleeve along said second half of said length, and a frictional retaining element integrally formed with said cylindrical body between said first and second ends for exerting a bearing force against said surface of the bone drill, said frictional retaining element includes a plurality of spring elements, said first and second halves of said cylindrical body meet at a middle portion of said body, and said plurality of spring elements of said frictional retaining element are positioned at said middle portion,
said drill sleeve having a weight and said bearing force of said frictional retaining element being sufficiently large to support at least the weight of said drill sleeve on said bone drill so as to hold a longitudinal position of said drill sleeve on said bone drill, and said bearing force being sufficiently small to allow longitudinal translation of said drill through said bore when said drill sleeve is held stationary.

18. A gauge system according to claim 17, wherein:
said body and said frictional retaining element of said gauge are together manufactured from one-piece of material.

19. A gauge system, comprising:
a) a bone drill having a shaft with a boring end, an opposite tool engaging end, a surface, and graduated indicia provided on said surface; and
b) a drill sleeve having a one-piece cylindrical body with a first end, a second end, a longitudinal axis extending therebetween, and a longitudinal bore extending along the longitudinal axis sized for passage of the bone drill, said drill sleeve being longitudinally symmetrical such that said first end is structurally identical to said second end, and a frictional retaining element integrally formed with said cylindrical body for exerting a bearing force against said surface of the bone drill, said frictional retaining element includes a plurality of spring elements spaced about a periphery of said bore and in contact with said surface of said drill,
said drill sleeve having a weight and said bearing force of said frictional retaining element being sufficiently large to support at least the weight of said drill sleeve on said bone drill so as to hold a longitudinal position of said drill sleeve on said bone drill, and said bearing force being sufficiently small to allow longitudinal translation of said drill through said bore when said drill sleeve is held stationary,
wherein a depth of a hole drilled by said bone drill is determined by referencing a location of said drill sleeve relative to said indicia on said bone drill, and given said longitudinal symmetry of said drill sleeve said depth is determinable regardless of whether said first end or said second end of said drill sleeve is advanced first over said bone drill.

20. A gauge system according to claim 19, wherein:
said plurality of spring elements are positioned in a middle portion of said cylindrical body.

21. A gauge system according to claim 19, further comprising:
a bone plate having a thickness and a screw hole extending through said plate in a direction of said thickness; and
a drill guide having a cylindrical bore, a distal end fixed in said hole, and a proximal end, said drill guide having a length extending from said plate to said proximal end,
wherein said drill sleeve is seated on said proximal end of said drill guide.

* * * * *